(12) United States Patent
Abe et al.

(10) Patent No.: US 7,883,523 B2
(45) Date of Patent: Feb. 8, 2011

(54) LANCET ASSEMBLY

(75) Inventors: Teruyuki Abe, Tokyo (JP); Kazuharu Seki, Tokyo (JP)

(73) Assignee: Izumi-Cosmo Company, Limited, Osaka (JP)

( * ) Notice: Subject to any disclaimer, the term of this patent is extended or adjusted under 35 U.S.C. 154(b) by 334 days.

(21) Appl. No.: 11/596,711

(22) PCT Filed: May 16, 2005

(86) PCT No.: PCT/JP2005/008899

§ 371 (c)(1),
(2), (4) Date: Jan. 8, 2007

(87) PCT Pub. No.: WO2005/110225

PCT Pub. Date: Nov. 24, 2005

(65) Prior Publication Data

US 2007/0225742 A1  Sep. 27, 2007

(30) Foreign Application Priority Data

May 17, 2004 (JP) .............................. 2004-146321

(51) Int. Cl.
*A61B 17/32* (2006.01)

(52) U.S. Cl. ...................................... 606/182; 606/181

(58) Field of Classification Search ................ 606/181, 606/182; 604/136, 110, 111, 192, 195; 600/580; 83/397–398; 401/134; 220/212, 810, 254.1, 220/200; 222/52, 526, 83, 83.5; 206/363, 206/364, 365

See application file for complete search history.

(56) References Cited

U.S. PATENT DOCUMENTS 4,442,836 A * 4/1984 Meinecke et al. ........... 606/182
4,677,979 A * 7/1987 Burns ......................... 606/172
4,869,249 A * 9/1989 Crossman et al. ........... 606/182
5,439,473 A * 8/1995 Jorgensen .................... 606/182
5,628,765 A * 5/1997 Morita ........................ 606/182
5,755,733 A * 5/1998 Morita ........................ 606/182
6,358,265 B1 * 3/2002 Thorne et al. ............... 606/181
6,616,616 B2   9/2003 Fritz et al.
7,150,755 B2  12/2006 LeVaughn et al.

(Continued)

FOREIGN PATENT DOCUMENTS

| JP | 2002-143132 | 5/2002 |
| JP | 2003-153885 | 5/2003 |
| WO | 96/16599 | 6/1996 |
| WO | 03/070099 | 8/2003 |
| WO | 03/071940 | 9/2003 |

OTHER PUBLICATIONS

Japanese Office Action issued Aug. 17, 2010 in corresponding Japanese Application No. 2006-513589.

*Primary Examiner*—(Jackie)Tan-Uyen T Ho
*Assistant Examiner*—David Eastwood
(74) *Attorney, Agent, or Firm*—Wenderoth, Lind & Ponack L.L.P.

(57) ABSTRACT

The present invention provides a lancet assembly which eliminates the need to remove a resin cover encapsulating a pricking element. Upon inserting a lancet structure into a lancet holder, a force which separates a lancet cover encapsulating the sharp tip portion of the pricking element from a lancet body is generated, and this force is allowed to act on the lancet cover and the lancet body to thereby expose, within the lancet holder, the sharp tip portion of the pricking element encapsulated by the lancet cover and to locate the opening of the lancet holder in front of the sharp tip portion of the pricking element.

37 Claims, 15 Drawing Sheets

U.S. PATENT DOCUMENTS

| | | |
|---|---|---|
| 2003/0050573 A1 | 3/2003 | Kuhr et al. |
| 2004/0092997 A1* | 5/2004 | Levin et al. .................. 606/181 |
| 2004/0243164 A1* | 12/2004 | D'Agostino ................. 606/181 |
| 2005/0015020 A1 | 1/2005 | LeVaughn et al. |
| 2005/0021066 A1 | 1/2005 | Kuhr et al. |
| 2006/0178600 A1 | 8/2006 | Kennedy et al. |
| 2007/0088377 A1 | 4/2007 | LeVaughn et al. |
| 2007/0225742 A1* | 9/2007 | Abe et al. .................... 606/182 |

* cited by examiner

LANCET ASSEMBLY

TECHNICAL FIELD

The present invention generally relates to a pricking device such as a finger-pricking device or a lancet assembly, which is used to prick the skin so as to obtain a small amount of blood therefrom. In particular, the present invention pertains to a disposable lancet assembly which is easily handled.

BACKGROUND OF THE INVENTION

A variety of finger-pricking devices or lancet assemblies are commercially available for not only individual users but also hospitals, clinics and town doctors, and they are used so as to collect a small amount of blood. Such a device comprises a lancet which comprises an element having an acutely sharpened part, i.e. a pricking element (e.g. a needle-shaped element) to momentarily pierce the skin or form an incision so as to bleed a small amount of blood therefrom.

In such a lancet assembly, the sharp tip portion of the pricking element for incising the skin is sterilized beforehand in the course of the manufacturing of the same.

It is essential that the sterilized state of the lancet assembly should be reliably maintained so as not to be contaminated by an ambient atmosphere until it is used, and it is also essential that the pricking element of the lancet assembly should not be unnecessarily being exposed so as not to touch and injure a person or other ambient matters during handling of the assembly for its use.

In view of the above, there is proposed a lancet assembly which comprises a lancet structure having a pricking element whose sharp tip portion is sealed by a resin, and a lancet holder for use in combination with the lancet structure (see Patent Literature 1 described later).

In use of this lancet assembly, it is troublesome to remove a resin cover which seals the sharp tip portion of the pricking element by fingers of one hand, while holding the lancet assembly by fingers of the other hand. Thus, it is desirable to be able to eliminate such a cover-removing operation.

Patent Literature 1: WO 96/16599

DISCLOSURE OF THE INVENTION

Problem to be Solved by the Invention

A problem to be solved by the present invention is therefore to provide a novel lancet assembly which can solve the above mentioned problems of the prior art, namely lancet assembly which eliminates the removal of the resin cover from the pricking element.

Means to Solve the Problem

As a result of the present inventor's intensive studies so as to solve the above discussed problem, it has been discovered that the problem is solved by a lancet assembly wherein a lancet cover is automatically removed from a pricking element by applying the following force upon inserting a lancet structure into a lancet holder: a force which mutually moves a lancet body and a lancet cover sealing a sharp tip portion of the pricking element away from each other, or a force which displaces the lancet cover away from the lancet body.

In the first aspect of the present invention, there is provided a lancet assembly which comprises a lancet structure and a lancet holder for holding the lancet structure, wherein the lancet structure comprises an ejector and a lancet;

the ejector includes an arm, a spring, and a base to which the arm and the spring are attached, wherein said spring has a connector at its front end and being connected at its rear end to the base;

the lancet includes a lancet body, a lancet cover and a pricking element which extends through the lancet body and the lancet cover, and a sharp tip portion of the pricking element is encapsulated by the lancet cover;

the lancet body is connected to the connector; the lancet holder has, at its front end portion, an opening through which the sharp tip portion of the pricking element passes through; and which is characterized in that when the lancet structure is inserted into the lancet holder so as to move the base relatively toward the connector and thereby compress the spring, the lancet cover separates from the pricking element to expose the sharp tip portion of the pricking element which portion is encapsulated.

In the case where the above mentioned lancet assembly is used to collect an amount of blood, when the base of the lancet structure inserted into the lancet holder is pressed to complete the preparation for pricking, the sharp tip portion of the pricking element which has been encapsulated by the lancet cover is exposed within the lancet holder, so that the opening of the lancet holder is located directly before the sharp tip portion of the pricking element [namely, the lancet cover is shifted away from a locus which is formed upon pricking by of the lancet body having the exposed pricking element (in this meaning, the wording "directly" is used), with the result that the pricking can be carried out without any hindrance against the movement of the lancet body]. In other words, the sharp tip portion of the pricking element which portion has been encapsulated by the lancet cover is automatically exposed.

In one of the embodiments of the lancet assembly according to the present invention, the lancet cover is located in front of the arms; the lancet cover and the lancet body are integrated to each other through a weakened portion;

the connector is coupled to the lancet body; and when the base of the ejector is moved relatively toward the connector so as to compress the spring with a front end portions of the arms kept in contact with a rear side of the lancet cover, the lancet cover is separated from the lancet body at the weakened portion. After the separation, moving the lancet cover away from the lancet body exposes the sharp tip portion of the pricking element which has been encapsulated by the lancet cover.

In another embodiment of the lancet assembly according to the present invention, the lancet cover is located in front of the arms;

the lancet cover and the lancet body are present as independently separate members which are integrated to each other through the pricking element; the connector is coupled to the lancet body; and when the base of the ejector is moved relatively toward the connector so as to compress the spring with front end portions of the arms kept in contact with a rear side of the lancet cover, the lancet cover is moved away from the lancet body. After that, the lancet cover is further moved away from the lancet body, namely, from the pricking element and is finally removed from the pricking element to thereby expose the sharp tip portion of the pricking element encapsulated by the lancet cover.

When the arms of the ejector are moved forward while the sharp tip portion of the pricking element is in its exposed state, the lancet cover has been separated from the lancet body as described above, and the lancet cover in contact with the front ends of the arms is moved forward in an oblique direction (for example, moved forward in an oblique and upward direction or in an oblique and downward direction), so that the opening of the front end portion of the lancet holder is located in front of the exposed pricking element.

In one preferable embodiment of the lancet assembly according to the present invention, the front end portions of the arms are engaged with the lancet cover. With this arrangement, the lancet cover removed from the pricking element is still held in contact with the arms by the arms. For example, the front end portions of the arms have inwardly bent hook-like portions (or L-shaped portions), respectively, and the lancet cover has, at its sides, portions to be engaged with the hook-like portions. Arranged thus, the lancet cover removed from the pricking element can be constrained by the arms.

In a further embodiment of the lancet assembly according to the present invention, the lancet holder has a guiding means on an inner side wall of its front end portion;

the lancet cover has a guided means to be guided by the guiding means; and the guiding means and the guided means are allowed to so cooperate that the lancet cover can be moved forward in an oblique direction (e.g. an upwardly or downwardly oblique direction) when the separated lancet cover is moved forward by the arms which are moved forward.

Specifically, the lancet holder has, on an inner side wall of its front end portion, a slide portion extending forward in an oblique direction as the guiding means; and the lancet cover has a portion (e.g. a projecting portion) as the guided means which slides on the slide portion.

For example, the lancet cover has, on an inner side wall of its front end portion, a tapered portion as a slid portion of which width (or thickness) becomes narrower toward the forward direction, while the lancet holder has, on an inner side wall of its front end portion, a tapered portion as the slide portion of which width (or thickness) becomes wider toward the forward direction (i.e. a reversed tapered portion) and which allows the former tapered portion to slide thereon. With this arrangement, these tapered portions are slid on each other so as to move the separated lancet cover forward in the oblique direction.

In a further embodiment of the lancet assembly according to the present invention, the slide portion may be a convex or concave portion which has a slide surface extending forward in the oblique direction and which is provided on the inner side wall of the front end portion of the lancet holder, while the slid portion may be a convex portion which is provided on the side wall of the lancet cover.

It is preferable that the base, arm(s), spring and the connector of the ejector are formed integrally with one another, using a resin, preferably by the injection molding of the resin. The lancet body and the lancet cover are formed integrally with each other, using a resin, preferably by the injection molding of the resin, with the pricking element (or a piercing element, usually a stainless steel needle) inserted into both of them, to thereby provide a lancet. The lancet body and the lancet cover is connected to each other through a notched portion which is particularly preferable to function as the weakened portion.

In a further embodiment of the lancet assembly according to the present invention, the lancet body and the lancet cover may be formed as separate members, and the pricking element may be contained in these members. In this case, the lancet body and the lancet cover are spaced apart from each other, so that a mid portion of the pricking element is exposed between these members. In this regard, the ejector and the lancet are independent and separate ones, which are preferably connected and integrated to each other through a connector. In a further embodiment, the ejector and the lancet may be formed as a single piece member as a whole, for example, by the injection molding so that they are originally integrated.

The resin to be used to form the ejector and the lancet, and the lancet holder is preferably a resin which can be used for injection molding. Specific examples of such a resin include POM (polyacetal resins), PBT (polybutyleneterephthalate resins), polyester copolymer resins, ABS resins, polycarbonate resins, polystyrene resins, polyethylene resins and polypropylene resins.

In the lancet assembly according to the present invention, the lancet holder further has a trigger which fires (or injects) the lancet body comprising the pricking element with its sharp tip portion exposed, after the lancet cover has been separated; and the connector further has a projecting portion. When the lancet structure is inserted into the lancet holder, the projecting portion of the connector is brought into being in contact with a projecting portion located in front of and adjacent to the trigger, and this contact state prevents the connector from further moving forward, with the result that the spring can be compressed. The trigger is a member which disengages this contact state.

By pressing this trigger into the inside of the lancet holder from the outside, the contact of the projecting portion of the connector with the projecting portion of the lancet holder is disconnected, and the compressed spring momentarily expands, so that the lancet body momentarily moves forward, namely, the lancet body having the pricking element exposed at its sharp tip portion is fired. At this point of time, for example, a tip of a finger applied to the opening of the front end of the lancet holder is pricked by the sharp tip portion of the pricking element. When the force pressing the trigger is released, the trigger is restored to its original position. In this connection, in place of the projecting portion provided on the connector, a projecting portion may be provided on the spring, particularly its front end portion, or on the lancet body, particularly its rear end portion.

The term "forward or front(or backward or back)" used throughout the present description is based on the direction along which the pricking element is moved so as to prick an object. The term "upward or up(or downward or down)" used in the present description is based on a plane which is defined by the respective arms (i.e. a plane which includes straight lines when the arms are assumed to substantially be such straight lines along which the arms extend) and which includes a moving direction of the pricking element; and the direction along which the lancet cover obliquely moves is expressed by the term "upward or up", and the direction which is opposite the former direction is expressed by the term "downward or down", for convenience (see FIG. 1). In addition, a direction which is perpendicular to both of the forward or rearward direction and the upward or downward direction and which composes a rectangular coordinate system together with these directions is referred to as a lateral direction.

Preferably, the lancet assembly according to the present invention is provided as an assembly of the lancet structure with the lancet holder as described above or below in any of appropriate forms: for example, at least one portion of the lancet structure is inserted into the lancet holder to complete the lancet assembly. More preferably, the lancet structure is so combined with the lancet holder that a whole of the lancet is inserted into the lancet holder, and that the projecting portion of the connector is in contact with the trigger (with the proviso that the spring is not compressed). In this form, it is particularly preferable that the lancet structure cannot be pulled out from the lancet holder. In a further embodiment, the lancet structure has not been assembled with the lancet holder. This form may be called a lancet assembly kit which includes a lancet structure and a lancet holder, rather than a lancet assembly.

In the second aspect of the present invention, there are provided a lancet holder and a lancet structure which compose the above- or below-described lancet assembly according to the present invention. The present invention further provides a lancet and an ejector which compose such lancet structure. What are described above or below with respect to the lancet assembly according to the present invention are similarly applicable to the lancet holder and the lancet structure, as well as the lancet and the ejector.

EFFECT OF THE INVENTION

According to the lancet assembly according to the present invention, an operation cane be saved which is required for removing a resin cover with the conventional lancet assembly. This is because, when the lancet structure is inserted into the lancet holder to complete the preparation for pricking with the lancet assembly according to the present invention, the lancet cover is separated from the lancet body, and the sharp tip portion of the encapsulated pricking element is automatically exposed within the lancet holder.

DETAILED DESCRIPTION OF THE INVENTION

Figure 1:
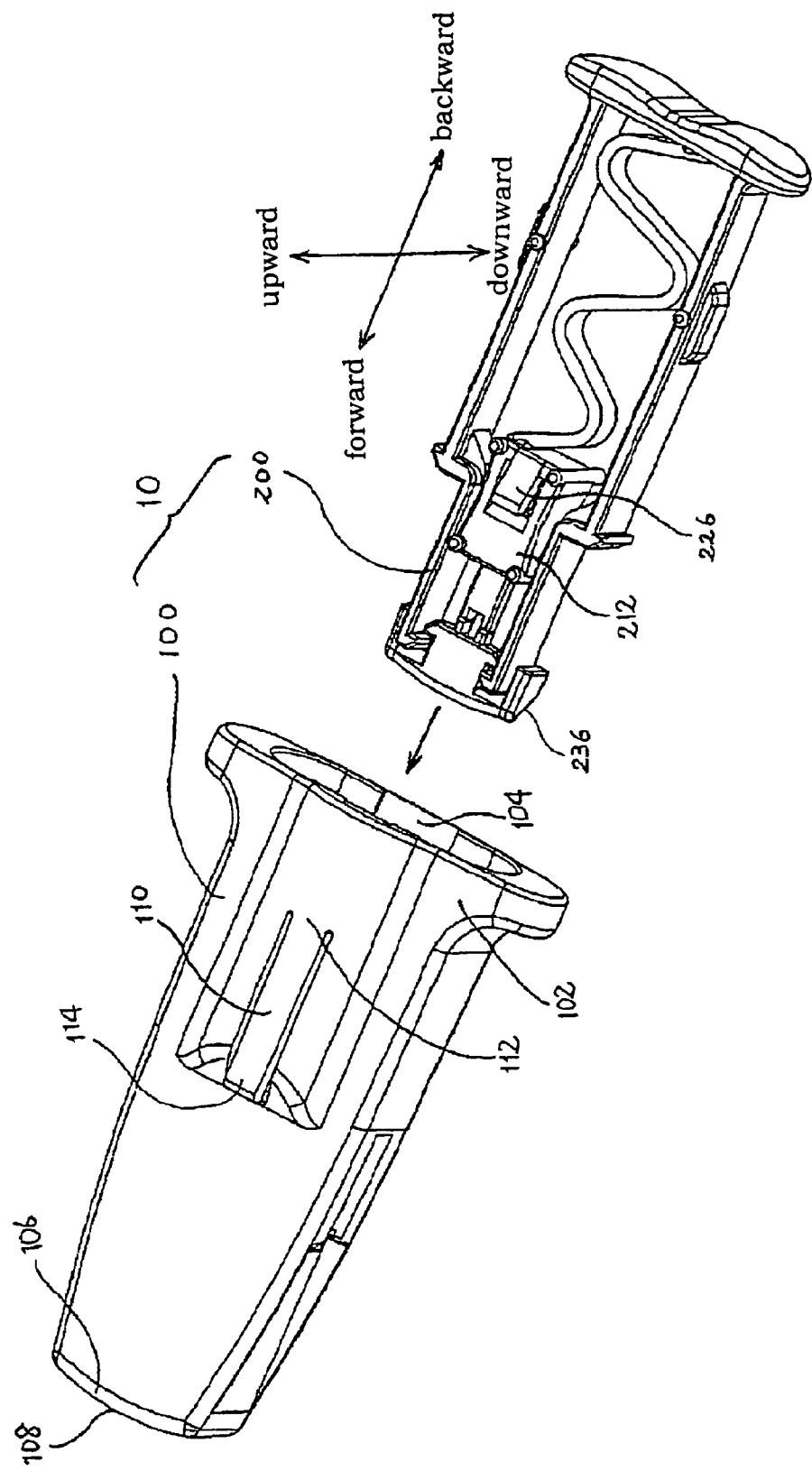
FIG. 1 shows a schematic perspective view of a lancet assembly according to the present invention, illustrating a condition of a lancet structure which has not yet been inserted into a lancet holder.

FIG. 1 shows a schematic perspective view of a lancet assembly 10 according to the present invention. The lancet assembly 10 comprises a lancet holder 100 and a lancet structure 200. FIG. 1 shows a condition of the lancet structure 200 just before being inserted into the internal space of the lancet holder 100 in the arrow direction. It is to be noted that FIG. 1 also indicates the present directions intended by the terms used in the present description, "forward or front", "backward", "upward or up" and "downward or down" which directions are based on a rectangular coordinate system.

The lancet holder 100 has an opening 104 in its rear end portion 102, and has an opening 108 (not shown in FIG. 1) in its front end portion 106. When an object to be pricked (for example, a tip of a finger) is pressed onto the opening 108 of the lancet holder, the object is pricked by an exposed sharp tip portion of a pricking element which thrusts through the opening 108. The lancet holder 100 has a trigger 110 in its upper surface. A rear end portion 112 of the trigger 110 is formed integrally with the body of the lancet holder 100, and a front end portion 114 of the trigger is so formed as to be pressed into the inside space of the lancet holder (in the downward direction in FIG. 1), and this front end portion restores its original form when a pressing force is eliminated. The lancet holder 100 has a projecting portion 116 (not shown in FIG. 1) on an inner surface of its upper side wall and just before the front end portion 114 of the trigger 110. Against this projecting portion 116 of the lancet holder 100 is abutted a projecting portion 226 of a lancet body 216 which will be described later, so that the lancet body 216 is prevented from moving forward. This prevented condition of the lancet body 216 is disengaged by pressing down the front end portion 114 of the trigger 110.

Figure 2:
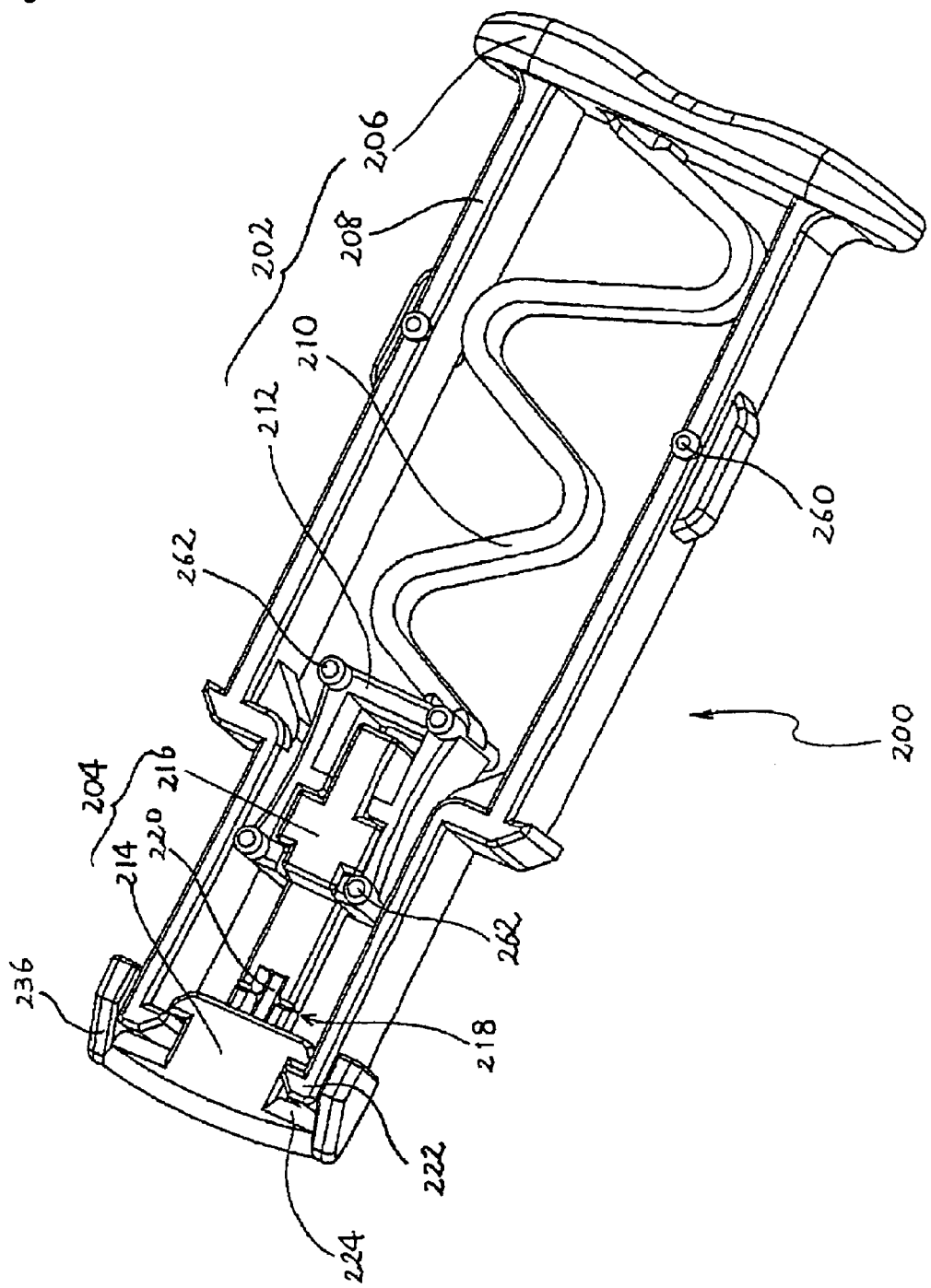
FIG. 2 shows a schematic perspective view of the lancet structure which is shown in FIG. 1 with turned upside down.

FIG. 2 shows a schematic perspective view of the reverse of the lancet structure 200 which is shown in FIG. 1 (namely, the lancet structure shown in FIG. 1 is turned upside down). The lancet structure 200 comprises an ejector 202 and a lancet 204. The ejector 202 includes a base 206 and arms 208 fixed to both sides of the base 206. As shown in FIG. 2, preferably, a spring is located between a pair of the arms as shown. In this regard, a single arm or three or more arms may be provided in the present invention. The spring 210 is located between or among these arms and is fixed at its one end to the base 206, and is fixed at its other end to a connector 212. Preferably, the base 206, the arms 206, the spring 210 and the connector 212 are formed integrally with one another, as described above. For example, these members can be formed by the injection molding of a resin.

The lancet 204 includes a lancet body 216 and a lancet cover 214 which are connected to each other through a weakened portion 218 as a notched portion (i.e. a V-shaped concavity). The lancet 204 further has a pricking element 220 whose sharp tip portion is encapsulated by the lancet cover 214. The rear end portion of the pricking element 220 is located within the lancet body 216. In the embodiment shown in FIG. 2, a portion of the pricking element 220 is exposed between the lancet body 216 and the lancet cover 214. It is noted that in another embodiment, no weakened portion may be provided, and, instead, the lancet body and the lancet cover as independent members may be disposed away from each other.

As is understood from FIG. 2, the lancet cover 214 is disposed in front of the arms 208, and the front end portions 222 of the arms 208 are in contact with the rear side 224 of the lancet cover 214 in the shown embodiment. In another embodiment, the front end portions of the arms may not be in contact with the rear side of the lancet cover, but may be disposed close to each other. Also in this embodiment, the front end portions 222 of the arms 208 can be brought into contact with the rear side 224 of the lancet cover 214, by further moving the arms 208 forward after the forward movement of the lancet body 216 is stopped, as described later.

Figure 3:
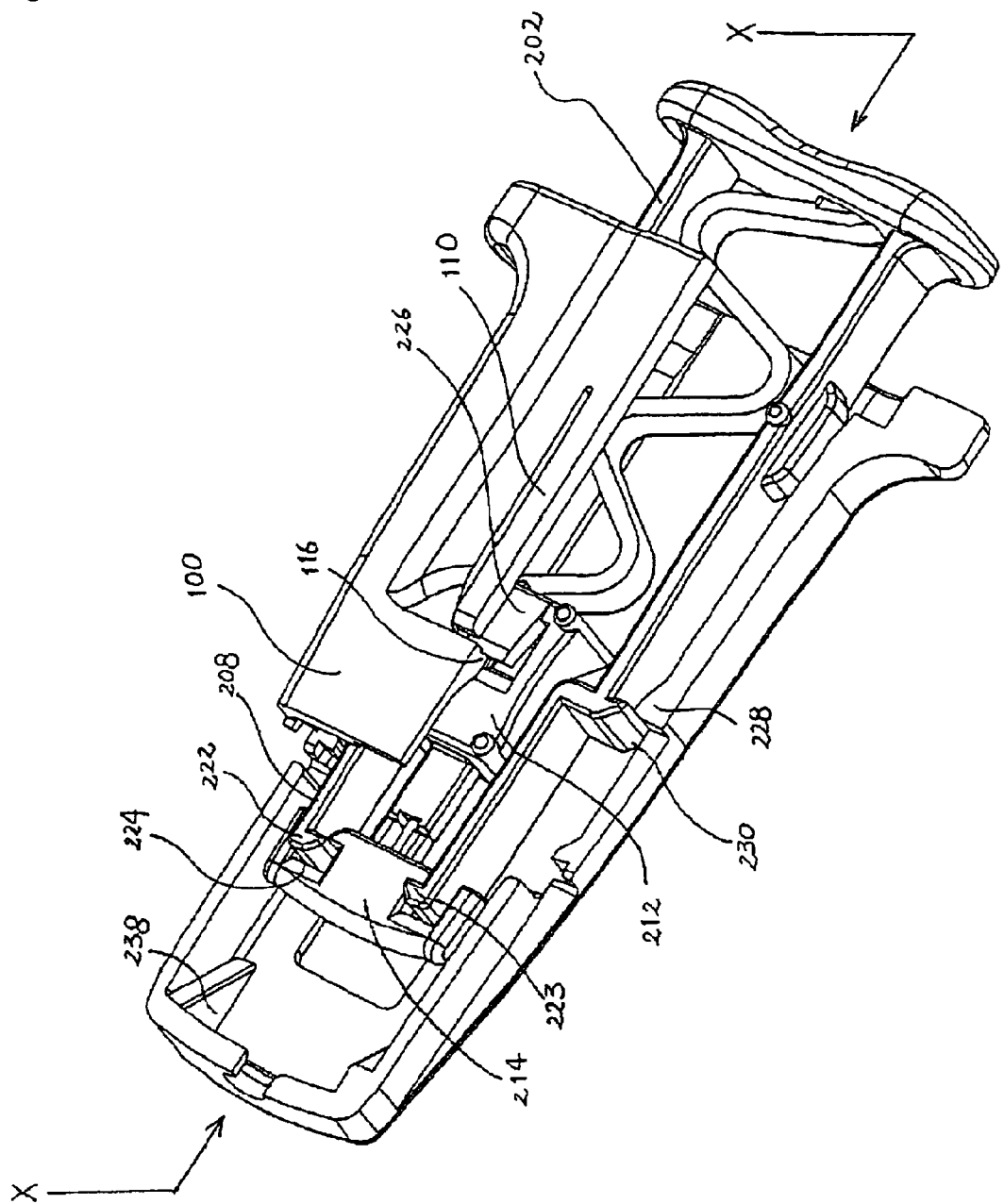
FIG. 3 shows a schematic perspective view of the lancet assembly according to the present invention, illustrating a condition under which a lancet body is prevented from moving forward by inserting the lancet structure into the lancet holder.

FIG. 3 shows a schematic perspective view of the lancet structure 200 inserted into the lancet holder 100. In this regard, FIG. 3 illustrates only the lower half portion and the rear half of the half of the upper half portion of the lancet holder 100 for better understanding the inside of the lancet holder 100, and other portions of the lancet holder are shown cut off. When the lancet structure 200 shown in the conditions as FIG. 1 is inserted into the lancet holder 100, the projecting portion 226 of the lancet body 216 is brought into contact with the projecting portion 116 formed on the upper inner wall of the lancet holder 100 in front of the trigger 110.

In FIG. 3, tapered projected portions 228, each having a width in the lateral direction becoming wider forward, are provided on the sides of the inner wall of the lancet holder, so that the reversely tapered projecting portions 230 (which have widths becoming narrower forward) provided at mid positions of the arms 208 can go over the tapered projecting portions 228 and move forward, while the lancet structure 200 is being inserted. Preferably, the tapered projecting portions 228 are so located that the projecting portion 226 of the connector can be brought into just contact with the projecting portion 116 of the lancet holder when the tapered projecting portions 230 have just gone over the tapered projecting portions 228.

Consequently, a user of the lancet assembly or a person who is assembling the lancet assembly can feel a snapping impact when the projected portion 226 of the connector has come into contact with the projected portion 116 of the lancet holder, and thus, advantageously, the user or such person recognizes this contact. Such a go-over movement of the tapered projecting portions becomes possible by making effective use of the elasticity of the resin of which the lancet structure and the lancet holder are formed, especially with respect to the projected portions. As is apparent from FIG. 3, by shaping these tapered projecting portions, after the tapered projecting portions 230 have once gone over the tapered projecting portions 228, it becomes substantially impossible for the tapered projecting portions 230 to again go back over the tapered projecting portions 228 and move rearward. As a result, it becomes substantially impossible to disintegrate the lancet assembly (or to pullout the lancet structure from the lancet holder) after the lancet assembly has been assembled or used, which is advantageous in that the reuse and misoperation of the lancet assembly can be avoided so that the safety of the lance assembly can be ensured.

Figure 4:
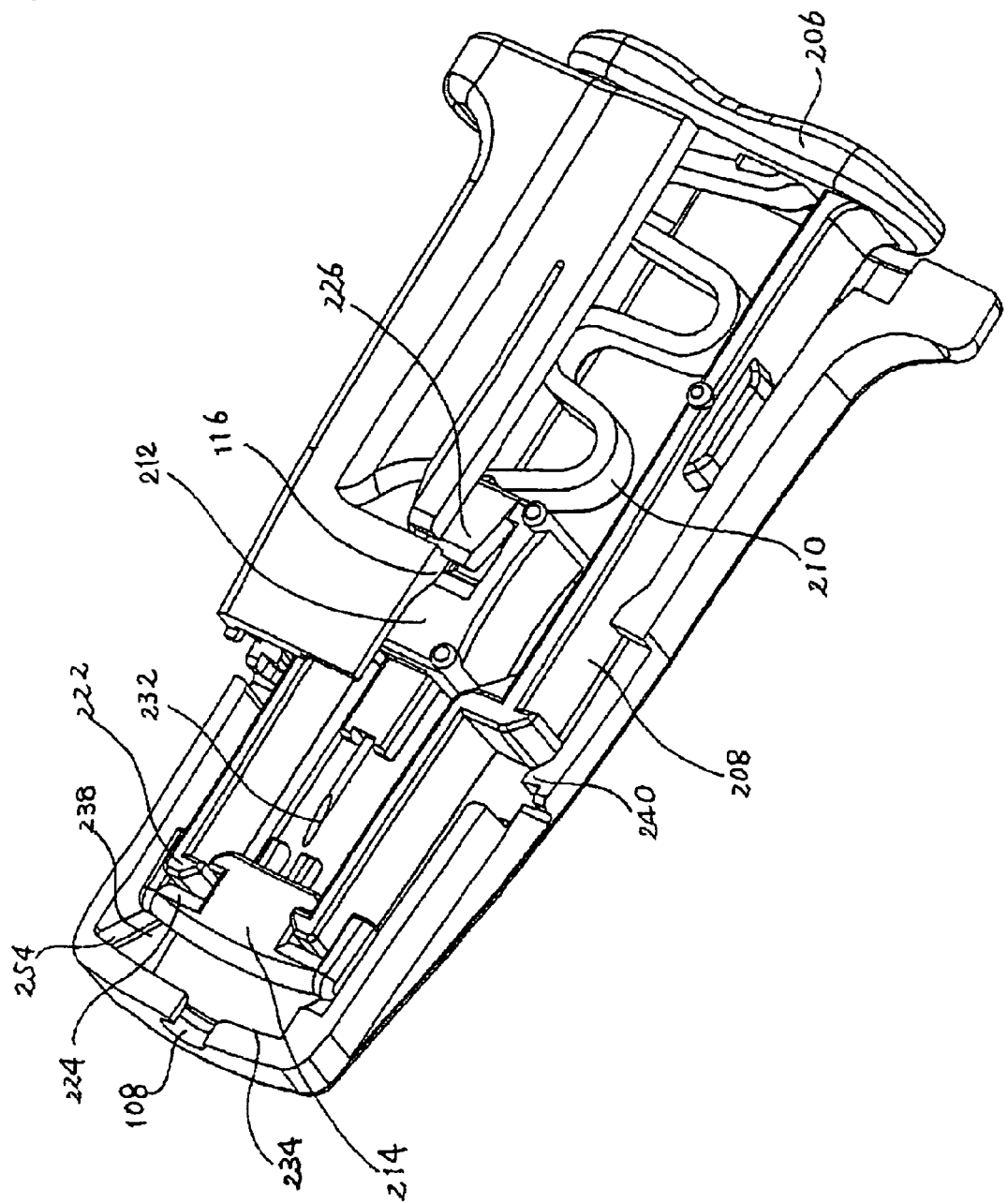
FIG. 4 shows a schematic perspective view of the lancet assembly according to the present invention, illustrating a condition under which the lancet cover is separated from the lancet body by further inserting the lancet structure under the condition shown in FIG. 3.

FIG. 4 shows a condition of the lancet structure 200 which is pressed forward by applying a force to the base 206 so as to further insert it. As is apparent from the comparison with FIG. 3, the spring 210 is compressible, and thus, the base 206 is moved forward, and the arms 208 are also moved forward, while the lancet body 216 is still located at the same position as shown in FIG. 3 since the lancet body 216 is in contact with the projecting portion 116 and thus is unable to move forward.

Since the front end portions 222 of the arms 208 are in contact with the rear side 224 of the lancet cover 214, the arms 208 are caused to apply a force to the lancet cover 214 which force is to move the lancet cover 214 forward when the lancet structure 200 in the condition shown in FIG. 3 is further pushed into. On the other hand, the lancet body 216 can not be moved forward since the projecting portion 116 of the lancet holder is in contact with the projecting portion 226 of the connector. As a result, such force acts to pull the lancet cover 214 and the lancet body 216 away from each other. Consequently, the lancet cover 214 and the lancet body 216 are pulled away from each other as shown in FIG. 4 to expose the sharp tip portion 232 of the pricking element 220. In this regard, if the lancet body and the lancet cover are disposed as independent separate members, the lancet cover is moved away from the lancet body, and finally, the sharp tip portion of the pricking element is exposed.

Figure 5:
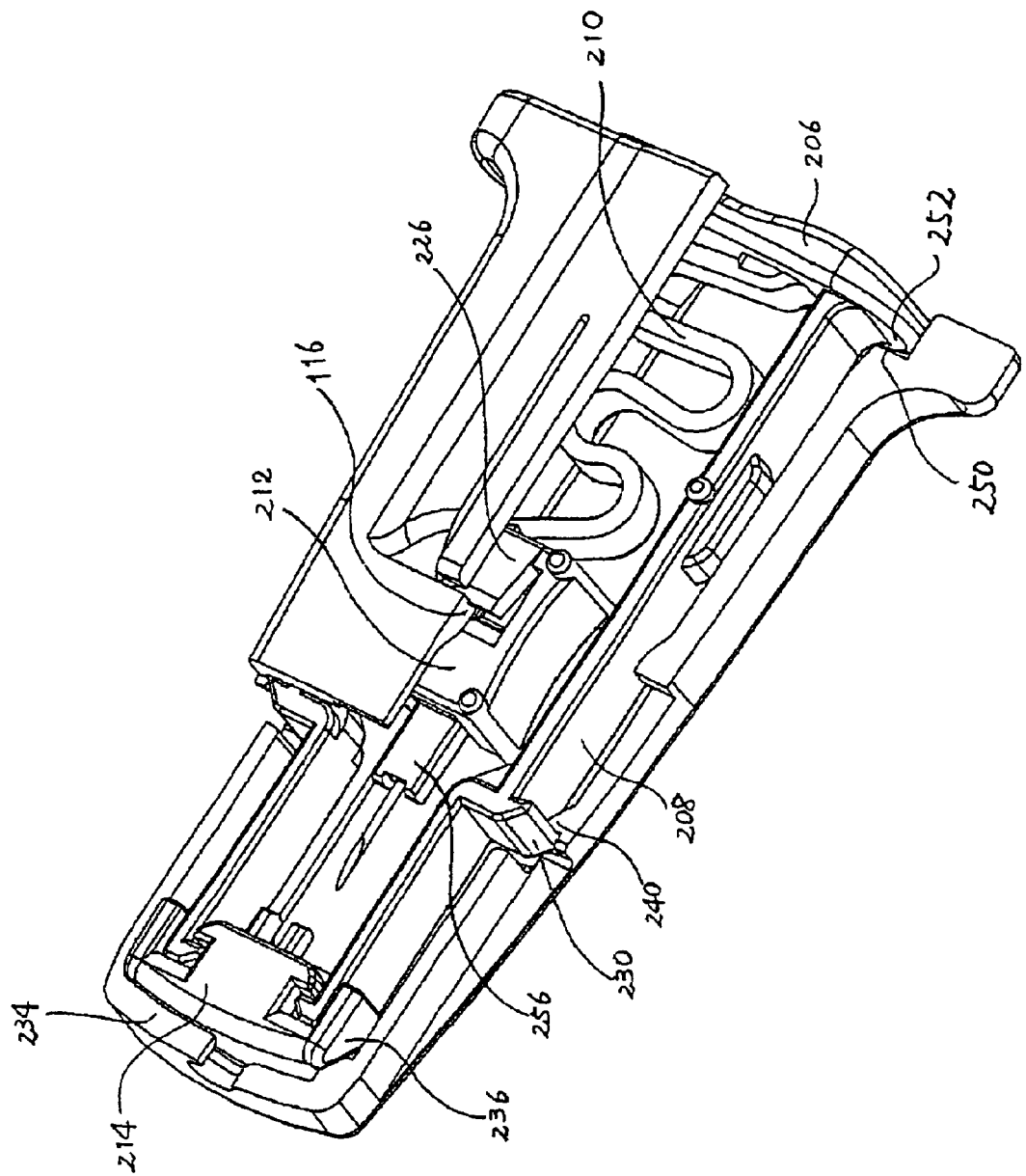
FIG. 5 shows a schematic perspective view of the lancet assembly according to the present invention, illustrating a condition under which the lancet cover is moved forward in an oblique and upward direction to be held by the front end portion of the lancet holder by further inserting the lancet structure under the condition shown in FIG. 4.

FIG. 5 shows a schematic perspective view of the lancet structure shown in FIG. 4 which is pushed forward by applying a force to the base 206 so as to further insert it. As is apparent from the comparison with FIG. 4, the arms are moved forward, while the lancet body 216 is unable to move forward because the projecting portion 226 of the connector is in contact with the projecting portion 116 of the lancet holder, and consequently, the lancet body 216 is located at the same position. However, the base has further been moved forward since the spring is compressible, and thus, both end portions 252 of the base are brought into contact with the stepped portions 250 provided around the opening of the rear end portion of the lancet holder, to thereby inhibit the further insertion of the lancet structure. It is noted that the projecting portion 226 is provided on the connector 212 in FIG. 5, but the projecting portion may be provided on the spring 210 or the lancet body 216.

As can be easily understood from FIGS. 3 and 4, it is preferable that the front end portions of the arms are configured to be able to engage with the lancet cover in the lancet assembly according to the present invention. More specifically, the front end portions 222 of the arms 208 have inwardly bent hook-like portions (or L-shaped portions) 223, respectively, and the lancet cover 222 have, at its both sides, portions to be engaged with these hook-like portions of the arms. In the shown embodiment, such portions have forms 225 which are complimentary to the hook-like portions 223 so that the former portions fit and match the latter portions (see FIG. 8). Since the front end portions of the arms are engaged with the lancet cover, the front end portions 222 of the arms 208 can be reliably kept in contact with the lancet cover 214 because of such engagement relationship between them, even after the pricking element 220 has been separated from the lancet cover 214. As a result, the lancet cover 214 can be moved backward together with the arms 208, even when the arms 208 are moved backward due to the action of the spring 210 which is caused, for example, by careless stopping of pushing the base 206 under the condition shown in FIG. 4 where the sharp tip portion 232 of the pricking element has been once exposed. If such an engagement relationship can not be ensured, the lancet cover is put in a free condition when the arms are moved backward, and it sometimes becomes difficult to ensure the contact between the front end portions 222 of the arms 208 and the lancet cover 214 when the arms are again moved forward. In this regard, it is apparent that the front end portions of the arms may be of any form other than the hook-like shape, so long as the front end portions of the arms can be engaged with the lancet cover.

As to the lancet assembly according to the present invention, what is to be particularly noted are as follows: the lancet holder has a guiding means on an inner side wall of its front end portion, and the lancet cover has a guided means to be led by the guiding means; and when the lancet cover separated by the cooperation of the guiding means and the guided means is moved forward by the arms which are moved forward, the lancet cover is moved forward in an oblique direction (an oblique and upward or downward direction). More specifically, the lancet holder has, as the guiding means, a slide portion extending forward in an oblique direction on the inner side wall of its front end portion; and the lancet cover has, as the guided means, a portion which slides on the above slide portion, such as a projecting portion.

As seen in FIG. 5, the separated lancet cover 214 is pushed by the arms 208, and comes into contact with the interior of the front wall 234 of the lancet holder. The lancet cover 214 has, at its sides, tapered portions 236 each having a width which is narrower in the vertical direction toward the front, as the guided means. On the other hand, the lancet holder 100 has, at the inner side wall of its front end portion, tapered portions 238 each of which has a width becoming wider toward the front (i.e. a reversed tapered portions) 238 as the guiding means. Each reversed tapered portion 238 as the guiding means has an inclining surface 254 as the slide portion (see FIG. 4). Underside surfaces of the tapered portions 236 of the lancet cover is allowed to slide on the inclined surfaces 254 of the reversed tapered portions 238. As a result, the tapered portions 236 of the lancet cover 214 pushed forward by the arms 208 are caused to climb the inclined surfaces 254 of the reversed tapered portions 238. In other words, the lancet cover 214 is moved forward in an oblique and upward direction by the arms 208, and comes into contact with the front wall 234 of the lancet holder. Such contact is ensured by keeping the arms 208 pushed.

Figure 14:
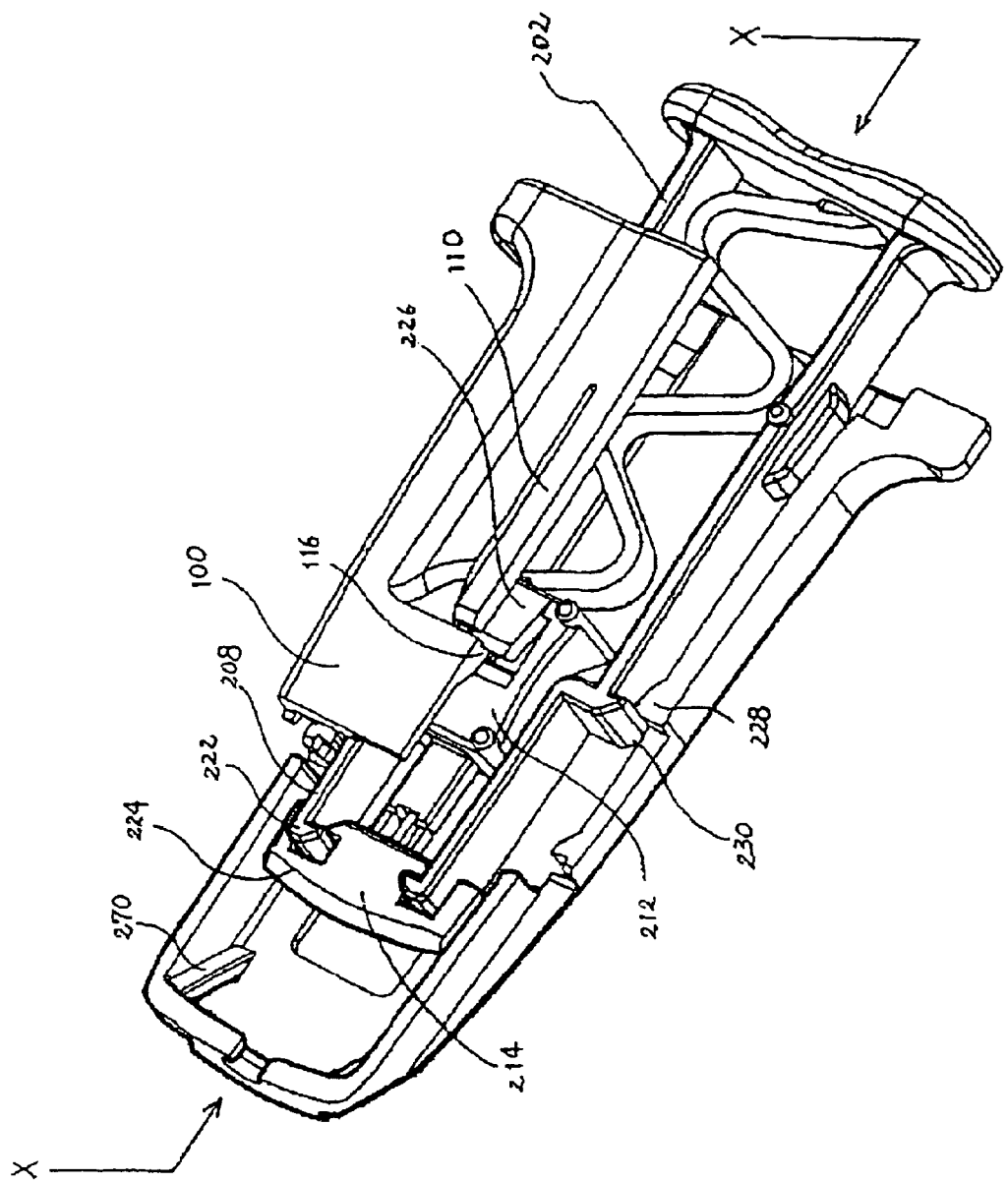
FIG. 14 shows a schematic perspective view of the lancet assembly similar to that shown in FIG. 3, illustrating another embodiment in which the lancet cover is moved forward in an oblique direction.
Figure 15:
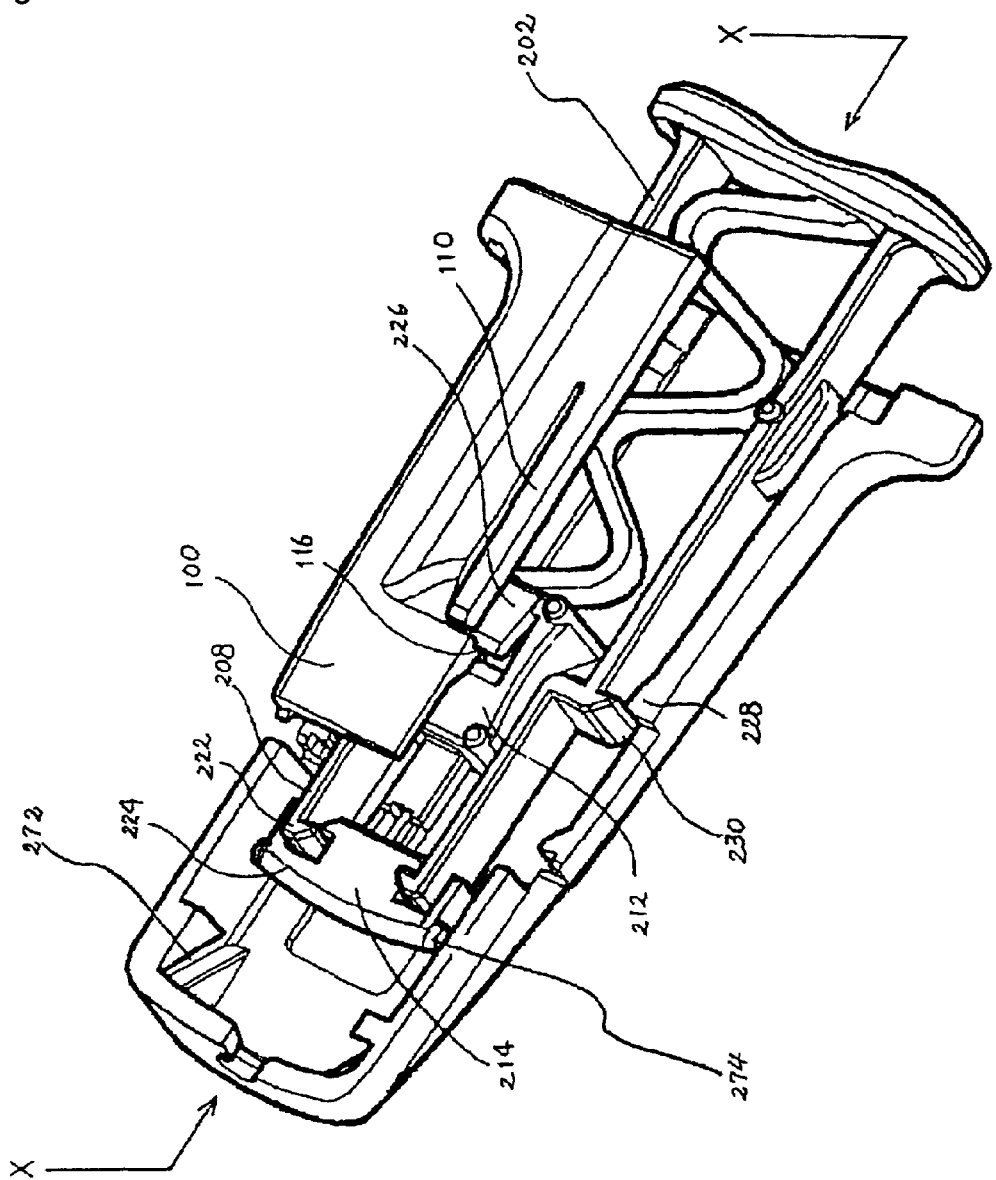
FIG. 15 shows a schematic perspective view of the lancet assembly similar to that shown in FIG. 3, illustrating a further embodiment in which the lancet cover is moved forward in an oblique direction.

Such movement of the lancet cover in the oblique direction can be achieved in one embodiment as shown in FIG. 14 wherein the slide portion is provided in the form of a convex portion or an inclined plate 270 having a sliding surface which extends forward in an oblique direction, and the slid portion is a side portion of the lancet cover or a convex portion provided on the side portion (the same one as a convex portion shown in FIG. 15).

In a further embodiment, the slide portion is provided in the form of, for example, a concave portion 272 having a sliding surface which extends forward in an oblique direction, and provided on an inner side wall of the front portion of the lancet holder, and the slid portion may be a convex portion 274 provided on the lancet cover, so that this convex portion can fall in the above concave portion and guided thereby.

In any of the foregoing cases, the movement of the lancet cover 214 in the oblique direction as described above is needed to be so sufficient that the exposed sharp tip portion 232 of the pricking element can pass through the opening 108 of the front end portion of the lancet holder 100 to surely prick a tip of a finger or the like. In other words, when the lancet body 216 whose pricking element has an exposed sharp tip portion 232 is fired, the lancet cover 214 is not located in front of the sharp tip portion 232 of the pricking element in the moving direction of the sharp tip portion 232, so that the lancet cover 214 never contacts the sharp tip portion 232 of the pricking element and never hinders the movement of the sharp tip portion of the pricking element (that is, the lancet cover 214 is not located on the moving locus which is formed by the movement of the sharp tip portion 232). In this sense, the term "direct" is used in the preceding paragraph.

When the lancet cover 214 is held by the front end portion of the lancet holder 100 as described above, the preparation for pricking is completed. In connection with this, the tapered projecting portions 240 having widths becoming wider forward in the lateral direction are provided on the side inner walls of the lancet holder (between the above-described projecting portions 228 and the front end portion of the lancet holder), so that the reversed tapered projecting portions 230 provided on mid points of the arms 208 are allowed to go over the tapered projecting portions 240 while the lancet structure 200 is inserted in the lancet holder. Preferably, the tapered projecting portions 240 are so located that the lancet cover 214 can just come into contact with the interior of the front wall 234 of the lancet holder when the tapered projecting portions 230 of the arms have gone over the tapered projecting portions 240.

As a result, because the user can feel a snapping impact when the above tapered projecting portions have come into contact with each other, the user conveniently knows that the preparation for pricking has been completed. Such a go-over movement of the tapered projecting portions becomes possible by making effective use of the elasticity of a resin of which the lancet structure and the lancet holder are formed. Further, as is apparent from the drawings, the projecting portions are tapered, and thus, it is substantially impossible for the projecting portions 230 to go over the projecting portions 240 and move backward, after the projecting portions 230 have once gone over the projecting portions 240. Consequently, it is practically impossible to disintegrate the lancet assembly after the use of the lancet assembly. Thus, the reuse and misoperation of the lancet assembly can substantially be avoided, and the safety as to the lancet assembly can be ensured.

Figure 6:
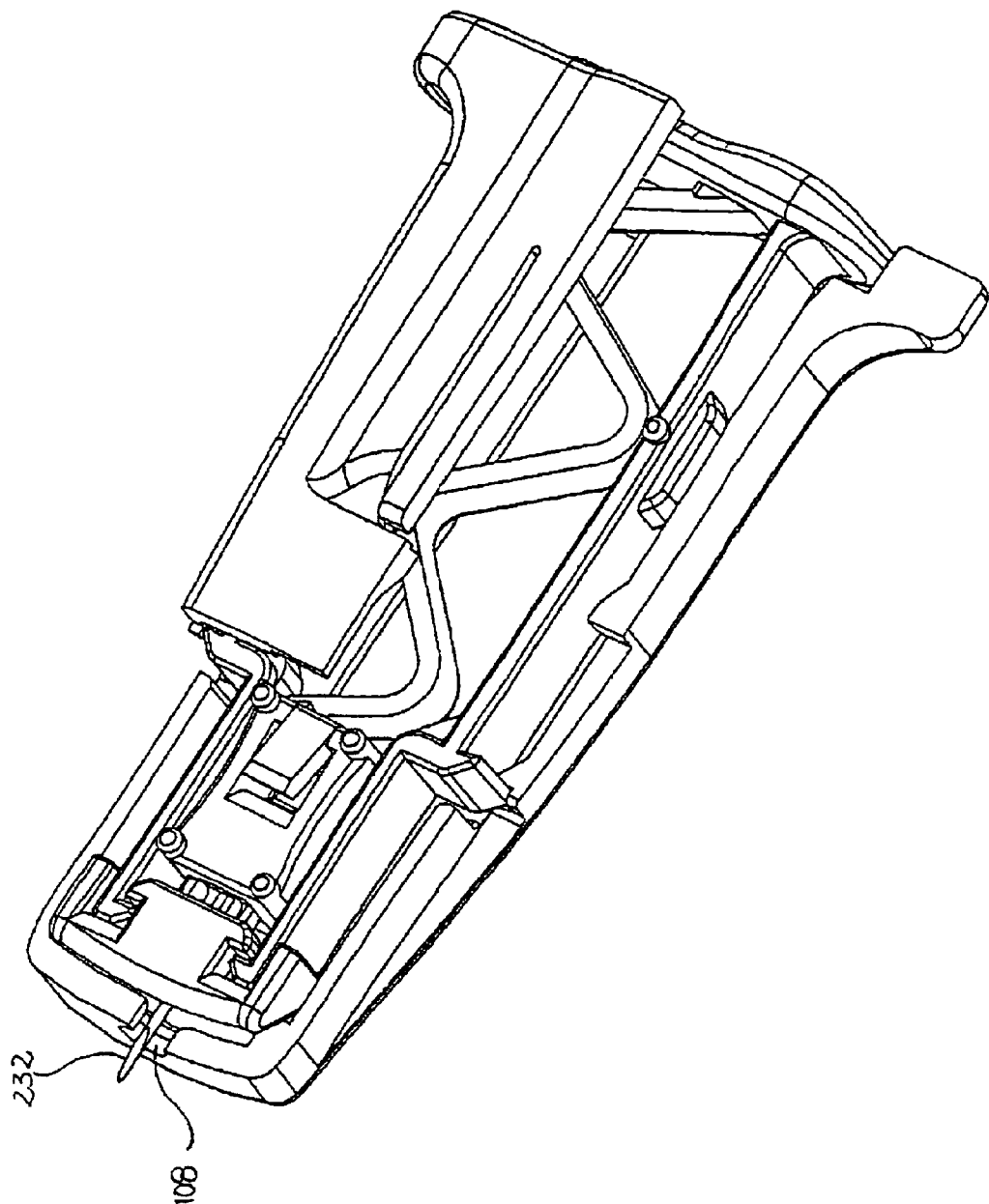
FIG. 6 shows a schematic perspective view of the lancet assembly of the present invention, illustrating a condition under which a sharp tip portion of a pricking element is being projected from an opening in a front end portion of the lancet holder, by releasing the lancet body from its constrained condition shown in FIG. 5.

The lancet assembly shown in FIG. 5 has been completely prepared for pricking. As is apparent from FIG. 5, the lancet body 216 is still in contact with the projecting portion 116 of the lancet holder located in front of the trigger 110. When the front end portion 114 of the trigger 110 is pushed into the lancet holder in this condition to thereby disengage such contact relationship between the projecting portion 116 and the projecting portion 226, the compressed spring 210 returns to its original form to thereby fire forward the lancet body 216 which comprises the pricking element having the exposed sharp tip portion, so that the sharp tip portion 232 of the pricking element can pass through the opening 108 without any hindrance by the lancet cover 214, to prick an object. FIG. 6 shows a schematic perspective view of the lancet assembly, illustrating the sharp tip portion of the pricking element has just protruded as described above. In this regard, since the spring 210 momentarily becomes free from its compressed and constrained condition, the spring expands longer as shown in FIG. 6 than the original length thereof shown in FIG. 1.

Figure 7:
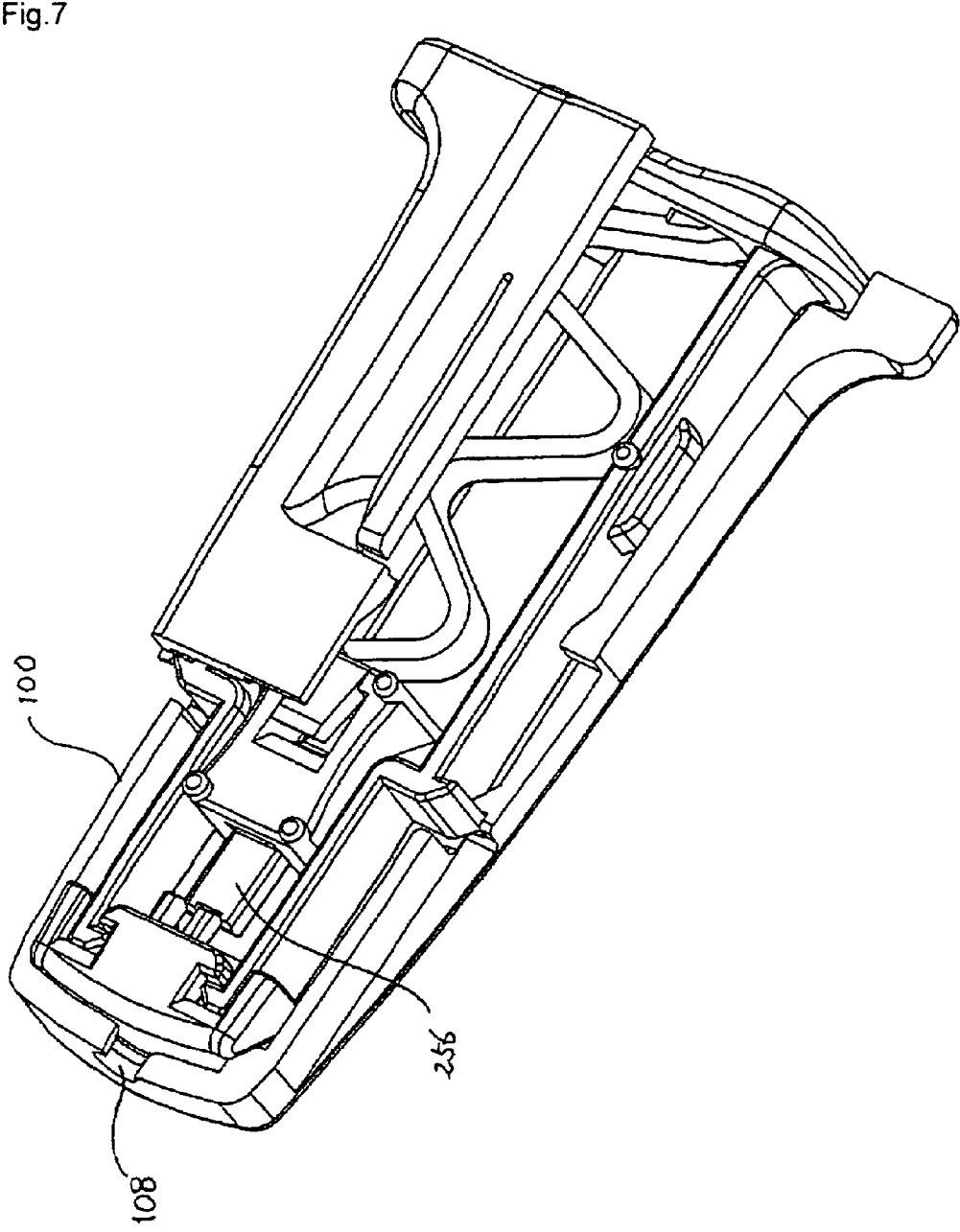
FIG. 7 shows a schematic perspective view of the lancet assembly according to the present invention, illustrating a condition under which a sharp tip portion of a pricking element has been retracted into the inside through the opening in the front end portion of the lancet holder while a spring shown in FIG. 6 has restored its original shape.

When the sharp tip portion 232 of the pricking element protrudes through the opening 108 of the lancet holder, it pricks a predetermined site of the object, and simultaneously, the front portion 256 of the lancet body 216 collides with the front wall of the lancet holder, so that the expanding spring 210 is about to restore. As a result, the spring is finally restored to its original form as shown in FIG. 2. The restored condition of the spring 210 is shown in FIG. 7. When the spring 210 has been restored, the sharp tip portion 232 of the pricking element is located at a position within the lancet holder sufficiently away from the opening of the lancet holder (not shown in FIG. 7, since the sharp tip portion 232 is located under the lancet cover 214). Therefore, the user can be practically protected from touching the sharp tip portion 232 of the pricking element exposed from the opening 108, from the outside of the lancet holder 100.

The lancet assembly shown in FIG. 7 has already been used for pricking, and this lancet assembly as it is can be discarded. As described above, the tapered-like projecting portions 230 and 240 make it impossible to draw out the lancet structure 200 from the lancet holder 100 in the condition shown in FIG. 7, and therefore, the sharp tip portion of the pricking element is never exposed even when the lancet assembly in the condition shown in FIG. 7 is discarded. Thus, the user can be protected from carelessly touching the sharp tip portion of the pricking element, and can discard it with improved safety.

In a preferable embodiment, each of the arms 208 has a projecting portion 260 as a guide pin as shown in the drawings. The guide pins are so designed to cooperate with channels which extend in the pricking direction on the inner surface of the lancet holder. That is, when the lancet structure is inserted into the lancet holder, the guide pins of the arms are allowed to slide in the channels of the lancet holder to smoothly move the arms forward within the lancet holder, so that the lancet structure can be smoothly inserted into the lancet holder. In other words, the guide pins of the arms lead the arms forward within the lancet holder.

In other preferable embodiment, the connector 212 has projecting portions 262 as guide pins as shown in the drawings, which cooperate with other channels extending in the pricking direction on the inner surface of the lancet holder. With this arrangement, when the lancet structure is inserted into the lancet holder, the guide pins of the connector are allowed to slide in the channels, so that the connector 212, i.e. the lancet body 216 coupled thereto can be smoothly moved forward to allow the smooth insertion of the lancet structure into the lancet holder. Further, these channels are useful to smoothly move the lancet body 216 forward and backward in the pricking direction within the lancet holder while the lancet body 216 is ejected out to prick the subject and then is retracted backward in order to withdraw the pricking element's sharp tip portion into the lancet holder. In other words, the guide pins of the connector lead the firing of the lancet body having the exposed pricking element.

The lancet structure according to the present invention comprises the ejector 202 and the lancet 204, both of which are integrally connected through the connector 212. Such connection may be carried out by any of appropriate methods: for example, one of a concave portion (or a female portion or a key hole portion) and a convex portion (or a male portion or a key portion) whose form is preferably complimentary to that of the other may be formed on the connector 212, and the other may be formed on the lancet body 216, so that the concave portion and the convex portion can be paired, matching each other. In this connection, the concave portion is formed on the connector and the convex portion is formed on the lancet body (or otherwise, they may be formed on the opposite members, respectively) such that the lancet body and the connector can mate each other for their engagement (or can separate from each other) while moving them in the upward or downward direction, but the lancet body and the connector can not separate from each other while moving them in the forward or backward direction. Alternatively, the concave portion is formed on the lancet body and the convex portion on the connector.

Figure 8:
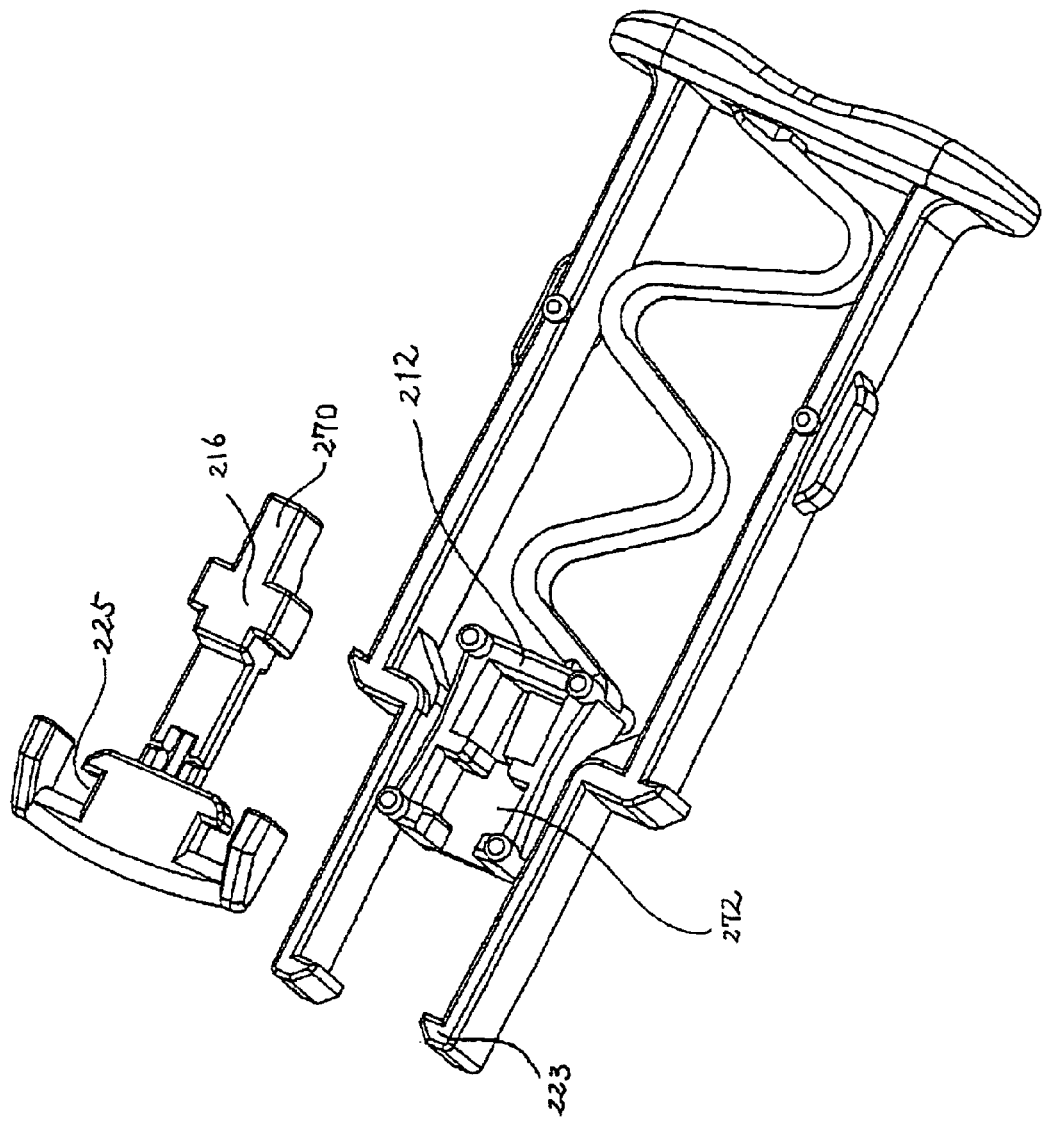
FIG. 8 shows an exploded perspective view of a lancet and an ejector which compose the lancet structure while they are shown in a disassembled condition.

FIG. 8 shows one example of such connections. As seen in FIG. 8, the lancet body 216 as a whole is formed to have a convex portion 270, and the connector 212 has a concave portion 272 into which the convex portion 270 of the lancet body fits. As can easily be understood, the convex portion 270 of the lancet body is moved downward to fit into the concave portion 272 of the connector, and then, the connector 212 and the lancet body 216 are not separated from each other against a force applied in the forward or backward direction, so that the connector 212 and the lancet body 216 can be operated together as one. However, the connector 212 and the lancet body 216 can be easily separated from each other by a force-applying thereto in the upward or downward direction. This connection method is advantageous, because the lancet and the ejector can be separately formed, and then they can be combined and integrated with each other.

Throughout the present description, the wording "becoming (become or be) narrower" or "becoming (become or be) wider" used to explain the tapered portion is based on when the lancet assembly is watched from its back side toward its front (i.e. the direction toward the front from the back in FIG. 1.). The wording "becoming narrower" is used to mean that the width of the tapered portion (the dimension vertical to the forward direction) becomes smaller, and the wording "becoming wider" is used to mean that the width of the tapered portion becomes larger. Further, the wording "the reversed tapered portion" means that such portion has a form which is reversed to that of a corresponding tapered portion. In other words, when one of tapered portions has a tapered form becoming narrower, and the other has a tapered form becoming wider, the former portion is referred to as having a tapered shape, and the latter is referred to as having a reversed tapered shape. On the contrary, when the latter is referred to as having a tapered shape, the former is referred to as having a reversed tapered shape. In addition, the wording "taper-like" also means the same as described above.

The pricking with using the lancet assembly according to the present invention is conducted as follows:

1) Firstly, the lancet structure 200 is inserted into the lancet holder 100 through the opening 104 at the rear end of the lancet holder (as indicated by the arrowhead direction on FIG. 1).

2) The lancet structure 200 is moved forward within the lancet holder 100, so that the front end of the projecting portion 226 formed on the lancet body 216 is brought into contact with the rear end of the projecting portion 116 formed as a stopper on the front side of the trigger 110 of the lancet holder 100. By doing so, the movement of the lancet 204 is stopped, and the lancet 204 is kept in a condition where no further forward movement is possible, namely, the lancet is constrained so as not to move forward (see FIG. 3).

3) The base 206 is further pressed forward while the lancet 204 is thus constrained, to thereby compress the spring 210 to which no force is applied, so that spring 210 accumulate an energy (i.e. a transition condition of the spring between the condition of the spring shown in FIG. 3 and that shown in FIG. 4).

4) The base 206 is further pressed into the lancet holder 100 so as to allow the arms 208 to push the lancet cover forward to thereby break the notched portion 218 (which functions as the weakened portion) as the connection between the lancet cover 214 and the lancet body 216, and thus, the lancet cover 214 is separated from the lancet body 216. After that, the arms 208 are further moved-forward to expose the sharp tip portion 232 of the pricking element (see FIG. 4).

5) When the arms are further moved forward, the lancet cover 214 is moved forward in the oblique and upward direction so as to be held in contact with the interior of the wall 234 of the front end portion of the lancet holder 100 (see FIG. 5).

6) Next, an object to be bled (for example, the tip of a finger) is pressed against the front opening 108 of the lancet holder.

7) The contact of the projecting portion 116 of the lancet holder with the projecting portion 226 of the lancet body is released by pressing the front end portion 114 of the trigger 110 into the inside of the lancet holder 100, and the compressed spring 210 momentarily expands to thereby fire forward the lancet body 216 so that the sharp tip portion 232 of the pricking element protrudes through the opening 108 to prick the object (see FIG. 6).

8) After that, the spring 210 returns to its original form, and the sharp tip portion 232 of the pricking element is retracted sufficiently away from the opening 108 (see FIG. 7).

FIGS. 9 to 13 show the schematic cross sectional views of the lancet assembly shown in FIGS. 3 to 7 respectively, taken along center line of the lancet holder (the line X-X), for the better understanding of the positional relationship of the lancet structure and the lancet holder of the present invention, and also the positional relationships of the components forming the structure and holder.

Figure 9:
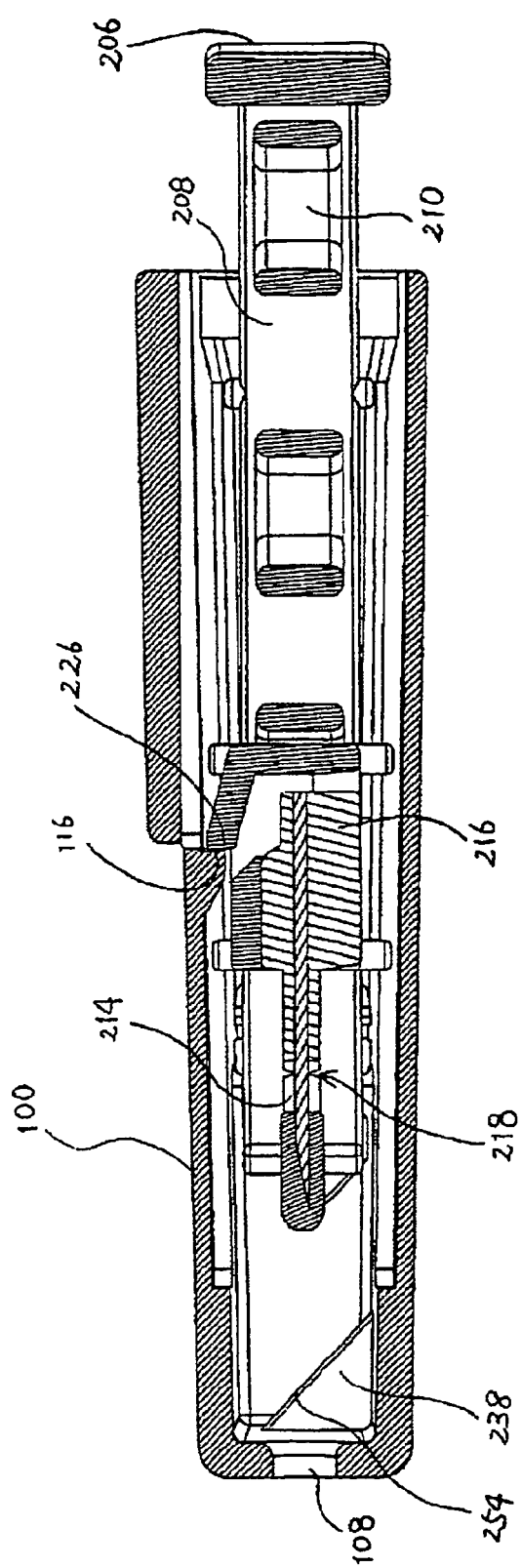
FIG. 9 shows a schematic sectional view of the lancet assembly shown in FIG. 3, taken along line X-X.

FIG. 9 shows the sectional view of the lancet assembly in the condition shown in FIG. 3. As seen in FIG. 9, the projecting portion 226 of the lancet body 216 is in contact with the projecting portion 116 located in front of the trigger 110 of the lancet holder 100. The lancet cover 214 and the lancet body 216 are connected and integrated to each other through the V-shaped notched portion 218.

Figure 10:
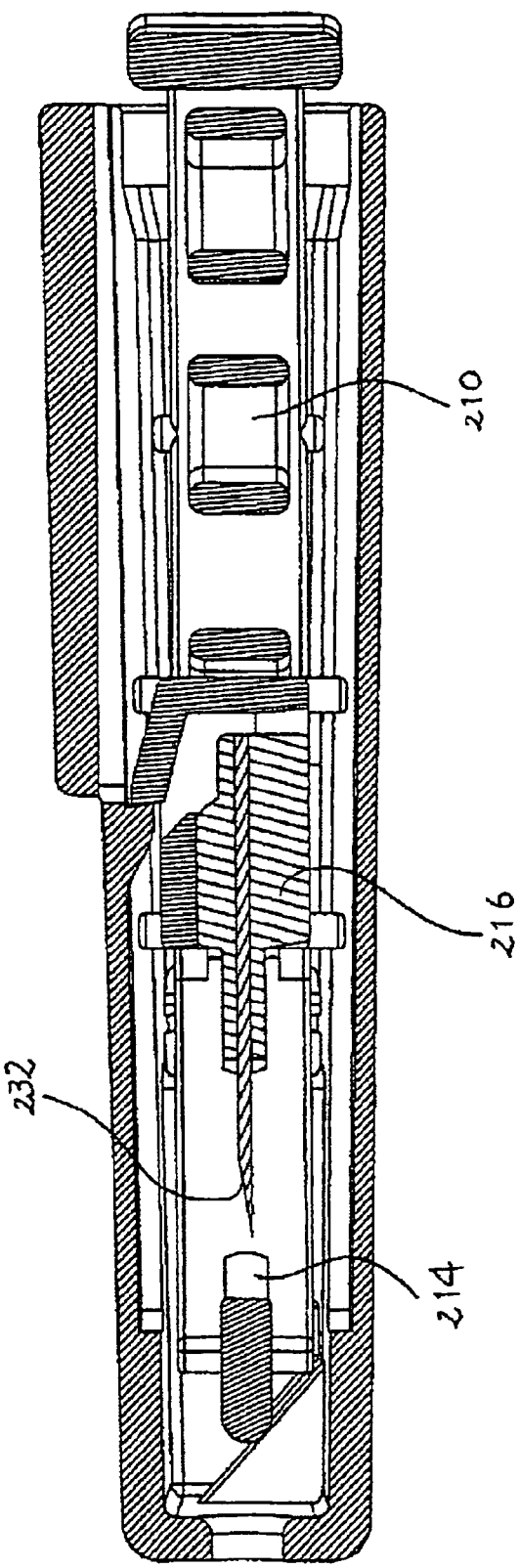
FIG. 10 shows a schematic sectional view of the lancet assembly shown in FIG. 4, taken in the same manner as in FIG. 9.

FIG. 10 shows the sectional view of the lancet assembly in the condition which corresponds to that shown in FIG. 4. As seen in FIG. 10, the lancet cover 214 is separated from the lancet body 216, so that the sharp tip portion 232 of the pricking element is exposed. It is also seen that the spring is compressed when compared with the spring shown in FIG. 9.

Figure 11:
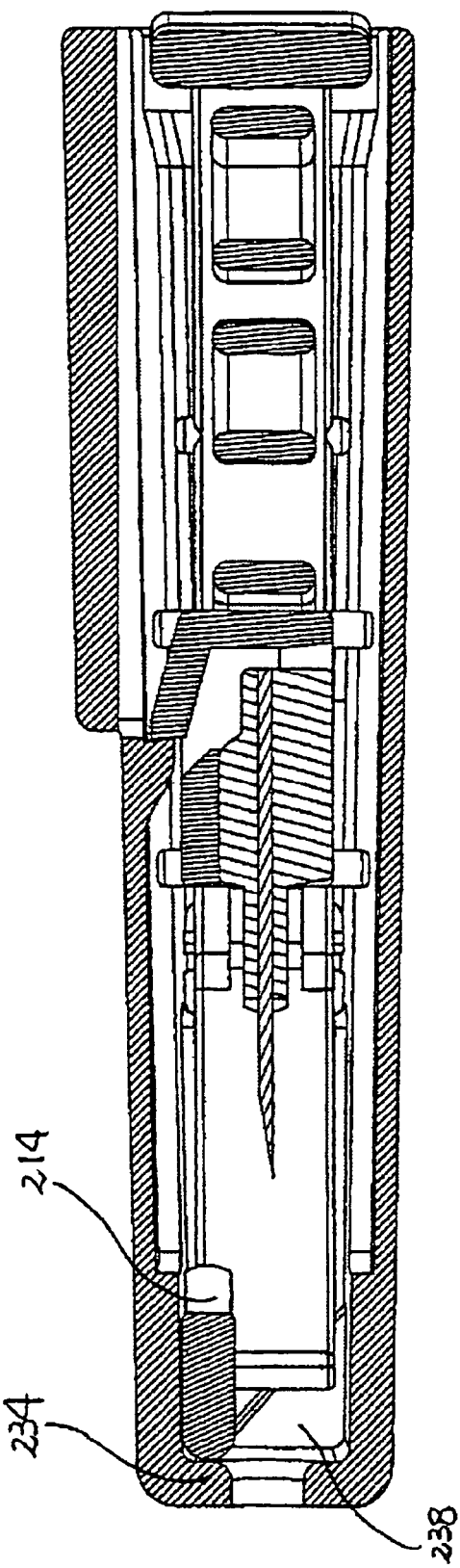
FIG. 11 shows a schematic sectional view of the lancet assembly shown in FIG. 5, taken in the same manner as in FIG. 9.

FIG. 11 shows the sectional view of the lancet assembly in the condition which corresponds to that shown in FIG. 5. In FIG. 11, the lancet cover 214 is in contact with the inner wall of the front end portion of the lancet holder. As seen in FIG. 11, the lancet cover has been moved not only forward but also upward, when compared with the lancet cover shown in FIG. 10: that is, the lancet cover has been moved forward in the oblique and upward direction. This is because the tapered portion 236 located on the side of the lancet cover is moved along the inclined surface 254 of the reversed tapered portion 238 located on the interior of the front end portion of the lancet holder.

Figure 12:
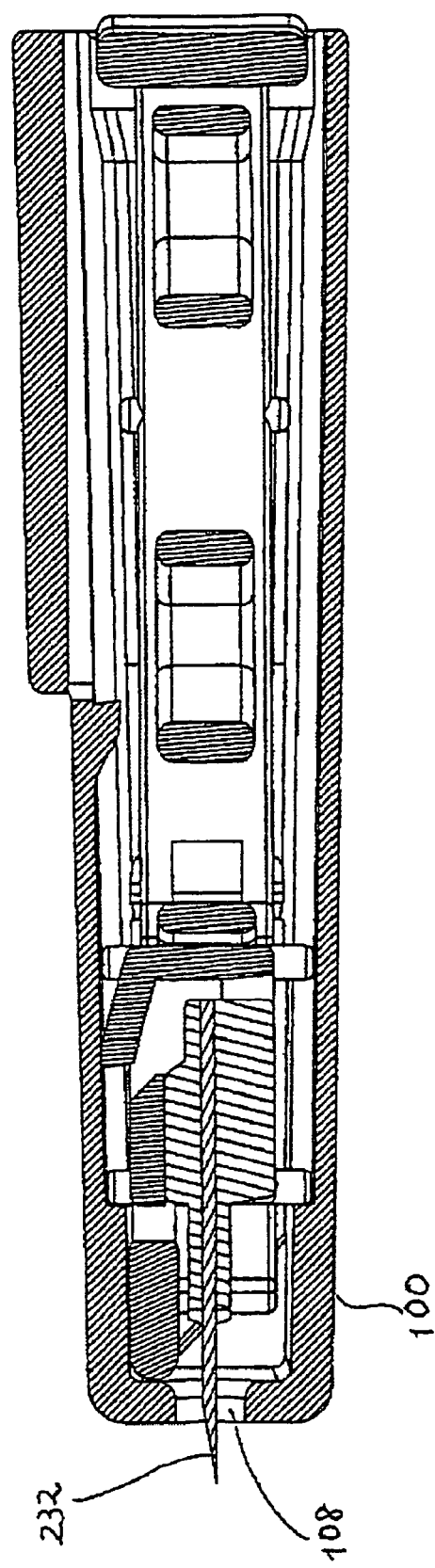
FIG. 12 shows a schematic sectional view of the lancet assembly shown in FIG. 6, taken in the same manner as in FIG. 9.

FIG. 12 shows the sectional view of the lancet assembly in the condition which corresponds to that shown in FIG. 6. In FIG. 12, the sharp tip portion 232 of the pricking element protrudes out through the opening 108 of the front end of the lancet holder 100. As is seen from FIG. 12, the movement of the pricking element is not hindered since the lancet cover 214 has already been moved forward in the oblique and upward direction.

Figure 13:
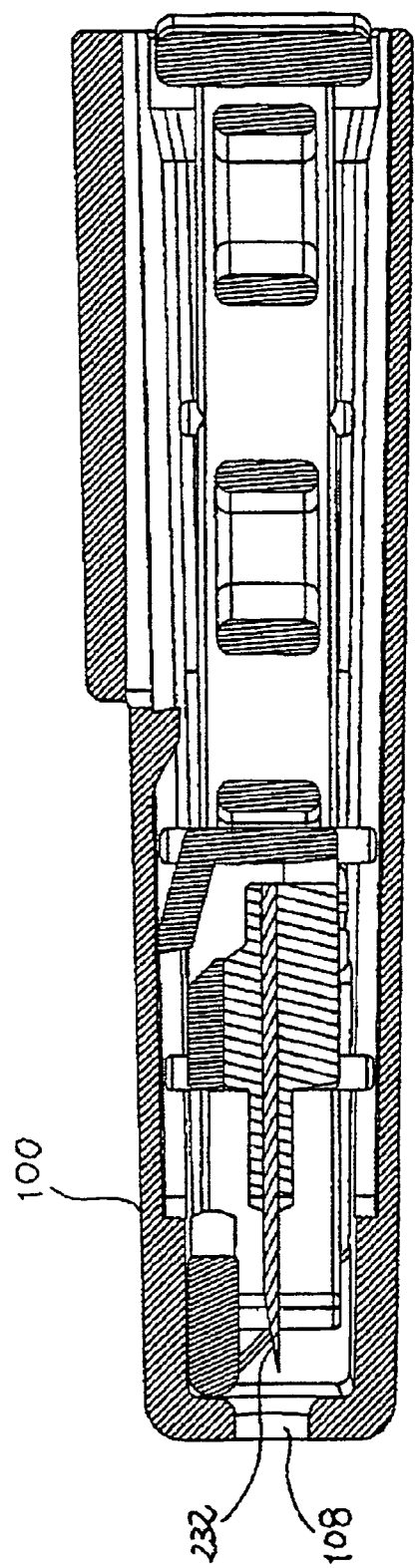
FIG. 13 shows a schematic sectional view of the lancet assembly shown in FIG. 7, taken in the same manner as in FIG. 9.

FIG. 13 shows the sectional view of the lancet assembly in the condition which corresponds to that shown in FIG. 7. In FIG. 13, the sharp tip portion 232 of the pricking element has been sufficiently retracted inside away from the opening 108 of the front end of the lancet holder 100. As seen from FIG. 13, it is quite hard for the user to touch the sharp tip portion 232 of the pricking element through the opening 108 of the lancet holder, and such touching is substantially impossible so long as the user does not willfully intend to touch the same.

INDUSTRIAL APPLICABILITY

The foregoing lancet assemblies according to the present invention provide more convenient blood-collecting means.

The invention claimed is:

1. A lancet assembly comprising:
   a lancet structure including an ejector and a lancet; and
   a lancet holder for holding the lancet structure, the lancet holder having a front end portion and a reverse tapered portion,
   wherein the ejector includes an arm, a spring having a front end and a rear end, and a base attached to the arm and the spring, the spring having a connector provided at the front end and being connected to the base at the rear end,
   wherein the lancet includes a lancet body, a lancet cover, and a pricking element, the lancet body being connected to the lancet cover, and the pricking element being disposed within the lancet body and the lancet cover such that a sharp tip portion of the pricking element is encapsulated by the lancet cover and such that the pricking element extends between the lancet body and the lancet cover, the lancet cover including a tapered portion,
   wherein the lancet body is connected to the connector,
   wherein an opening is provided at the front end portion of the lancet holder, the opening being configured to allow the sharp tip portion of the pricking element to pass therethrough, and wherein the lancet structure is configured to be inserted into the lancet holder such that the base moves toward the connector and the spring is compressed, and such that the lancet cover is separated from the pricking element by movement in an oblique direction of the lancet cover by the tapered portion of the lancet cover being moved along the reverse tapered portion of the lancet holder, relative to the pricking element, which remains substantially in the same position, thereby exposing the encapsulated sharp tip portion of the pricking element.

2. The lancet assembly of claim 1, wherein the lancet cover is configured to be automatically separated from the pricking element.

3. The lancet assembly of claim 1, wherein the arm of the ejector constitutes a first arm, and the ejector includes a second arm, and
   wherein said first arm and said second arm engage the lancet cover such that said lancet cover is separable from the lancet body, and such that movement of the ejector into the lancet cover automatically separates the lancet cover from the lancet body.

4. The lancet assembly of claim 1, wherein the arm of the ejector constitutes a first arm, and the ejector includes a second arm,
   wherein the first arm and the second arm engage the lancet cover such that said lancet cover is separable from the lancet body, and such that movement of the ejector into the lancet cover automatically separates the lancet cover from the lancet body.

5. The lancet assembly according to claim 1, wherein the pricking element is disposed in the lancet cover, and the lancet cover is arranged so as to be displaced laterally relative to a longitudinal direction of the pricking element when the spring is compressed so as to enable the pricking element to pass through the opening in the lancet holder.

6. The lancet assembly according to claim 1, wherein said lancet cover and said lancet body are integrally connected by a weakened portion located therebetween.

7. The lancet assembly according to claim 1, wherein said pricking element is held within said lancet cover and said lancet body, said lancet cover and said lancet body being independent and separate members.

8. The lancet assembly according to claim 6, wherein said lancet cover is located in front of the arm; and said lancet cover is configured to be separated, at the weakened portion, from said lancet body when the base is moved toward the connector to compress the spring while a front end portion of the arm is held in contact with a rear side of the lancet cover.

9. The lancet assembly according to claim 7, wherein said lancet cover is located in front of the arm; and said lancet cover is configured to be moved forward relative to said lancet body when the base is moved toward the connector to compress the spring while a front end portion of the arm is held in contact with a rear side of the lancet cover.

10. The lancet assembly according to claim 1, wherein a front end portion of the arm is engaged with the lancet cover such that contact between the arm and the lancet cover is maintained by the arm after the lancet cover is separated from the pricking element.

11. The lancet assembly according to claim 10, wherein the front end portion of the arm has an inwardly bent hook-like portion and the lancet cover has a portion which is engaged with the hook-like portion of the arm.

12. The lancet assembly according to claim 1, wherein the removed lancet cover is arranged to be moved forward in an oblique direction by the arm which is moved forward, so that the opening of the front end portion of the lancet holder is located in front of the exposed pricking element.

13. The lancet assembly according to claim 1, wherein the base, the arm, the spring and the connector of the ejector are integrally formed of a resin.

14. The lancet assembly according to claim 1, wherein the lancet body and the lancet cover are formed integrally with each other by molding a resin while the pricking element is inserted.

15. The lancet assembly according to claim 6, wherein the weakened portion is formed as a notched portion; and the lancet cover is separable from the lancet body and the pricking element by breaking the notched portion.

16. The lancet assembly according to claim 1, wherein the lancet body is formed in a shape complimentary to the connector and the connector is formed in a shape complimentary to the lancet body such that the lancet body can be engaged with the connector so as not to be separable in a pricking direction.

17. The lancet assembly according to claim 16, wherein the connector has a concave portion, and the lancet body has a convex portion which is engaged with said concave portion.

18. The lancet assembly according to claim 16, wherein the lancet body has a concave portion, and the connector has a convex portion which is engaged with said concave portion.

19. The lancet assembly according to claim 1, wherein the lancet body and the connector are originally formed integrally with each other.

20. The lancet assembly according to claim 1, wherein the lancet holder includes a trigger which fires the lancet body comprising the pricking element with the sharp tip portion exposed, and a projecting portion located in front of the trigger; and the connector has a projecting portion,
    whereby the projecting portion of the connector is brought into contact with the projecting portion of the lancet holder upon the compression of the spring such that the connector is inhibited from moving forward; and the trigger is operable to release such contact.

21. The lancet assembly according to claim 1, wherein the lancet holder includes a trigger which fires the lancet body comprising the pricking element with the sharp tip portion exposed, and a projecting portion located in front of the trigger; and the spring has a projecting portion,
    whereby the projecting portion of the spring is brought into contact with the projecting portion of the lancet holder upon the compression of the spring such that the connector is inhibited from moving forward; and the trigger is operable to release such contact.

22. The lancet assembly according to claim 1, wherein the lancet holder includes a trigger which fires the lancet body comprising the pricking element with the sharp tip portion exposed, and a projecting portion located in front of the trigger; and the lancet body has a projecting portion,
    whereby the projecting portion of the lancet body is brought into contact with the projecting portion of the lancet holder upon the compression of the spring such that the connector is inhibited from moving forward; and the trigger is operable to release such contact.

23. The lancet assembly according to claim 1, wherein the arm has a guide pin; and the lancet holder has, on an inner wall, a channel portion which leads the guide pin.

24. The lancet assembly according to claim 1, wherein the connector has a guide pin; and the lancet holder has, on an inner wall, a channel portion which leads the guide pin.

25. The lancet assembly according to claim 1, wherein the arm of the ejector is a first arm and the ejector includes a second arm, and a spring is provided between the first arm and the second arm.

26. A lancet structure which is for the production of a lancet assembly, said lancet structure comprising:
    an ejector; and
    a lancet,
    wherein the ejector includes an arm, a spring having a front end and a rear end, and a base attached to the arm and the spring, the spring having a connector provided at the front end and being connected to the base at the rear end,
    wherein the lancet includes a lancet body, a lancet cover, and a pricking element, the lancet body being connected to the lancet cover, and the pricking element being disposed within the lancet body and the lancet cover such that a sharp tip portion of the pricking element is encapsulated by the lancet cover and such that the pricking element extends between the lancet body and the lancet cover, the lancet cover including a tapered portion,
    wherein the lancet body is connected to the connector, and
    wherein the lancet structure is configured to be inserted into a lancet holder such that the base moves toward the connector and the spring is compressed, and such that the lancet cover is separated from the pricking element by movement in an oblique direction of the lancet cover by the tapered portion of the lancet cover being moved along a reverse tapered portion of the lancet holder, relative to the pricking element, which remains substantially in the same position, thereby exposing the encapsulated sharp tip portion of the pricking element.

27. A lancet holder which is for the production of a lancet assembly including a lancet structure, wherein an opening is provided at a front end portion of said lancet holder, the opening being configured to allow a sharp tip portion of a pricking element of the lancet structure to pass therethrough, and
    wherein the lancet holder is configured to receive the lancet structure therein such that a base of the lancet structure moves toward a connector of the lancet structure and a spring of the lancet structure is compressed, and such that a lancet cover of the lancet structure is separated from the pricking element of the lancet structure by movement in an oblique direction of the lancet cover by a tapered portion of the lancet cover being moved along a reverse tapered portion of the lancet holder, relative to the pricking element, which remains substantially in the same position, thereby exposing the encapsulated sharp tip portion of the pricking element.

28. A lancet which is for the production of a lancet structure, said lancet comprising:

a lancet body;

a lancet cover including a tapered portion; and a pricking element, wherein said lancet body is connected to said lancet cover, and said pricking element is disposed within said lancet body and said lancet cover such that a sharp tip portion of said pricking element is encapsulated by said lancet cover and such that said pricking element extends between said lancet body and said lancet cover, and wherein said lancet is configured to be inserted into a lancet holder such that such that said lancet cover is separated from said pricking element by movement in an oblique direction of said lancet cover by said tapered portion of said lancet cover being moved along a reverse tapered portion of the lancet holder, relative to said pricking element, which remains substantially in the same position, thereby exposing the encapsulated sharp tip portion of said pricking element.

29. An ejector which is for the production of a lancet structure, said ejector comprising:

an arm;

a spring having a front end and a rear end; and a base attached to said arm and said spring, wherein said spring has a connector provided at said front end and is connected to said base at said rear end, and wherein said ejector is configured to be inserted into a lancet holder such that said base moves toward said connector and said spring is compressed, and such that a lancet cover of the lancet structure is separated from a pricking element of the lancet structure by movement in an oblique direction of the lancet cover by a tapered portion of the lancet cover being moved along a reverse tapered portion of the lancet holder, relative to the pricking element, which remains substantially in the same position, thereby exposing an encapsulated sharp tip portion of the pricking element.

30. A kit of a lancet assembly which includes a lancet structure and a lancet holder, wherein:

the lancet structure includes an ejector and a lancet, and the lancet holder is provided for holding the lancet structure, the lancet holder having a front end portion and a reverse tapered wherein the ejector includes an arm, a spring having a front end and a rear end, and a base attached to the arm and the spring, the spring having a connector provided at the front end and being connected to the base at the rear end, wherein the lancet includes a lancet body, a lancet cover, and a pricking element, the lancet body being connected to the lancet cover, and the pricking element being disposed within the lancet body and the lancet cover such that a sharp tip portion of the pricking element is encapsulated by the lancet cover and such that the pricking element extends between the lancet body and the lancet cover, the lancet cover including a tapered portion, wherein the lancet body is connected to the connector, wherein an opening is provided at the front end portion of the lancet holder, the opening being configured to allow the sharp tip portion of the pricking element to pass therethrough, and wherein the lancet structure is configured to be inserted into the lancet holder such that the base moves toward the connector and the spring is compressed, and such that the lancet cover is separated from the pricking element by movement in an oblique direction of the lancet cover by the tapered portion of the lancet cover being moved along the reverse tapered portion of the lancet holder, relative to the pricking element, which remains substantially in the same position, thereby exposing the encapsulated sharp tip portion of the pricking element.

31. A kit of a lancet structure which includes a lancet and an ejector, wherein the ejector includes an arm, a spring having a front end and a rear end, and a base attached to the arm and the spring, the spring having a connector provided at the front end and being connected to the base at the rear end, wherein the lancet includes a lancet body, a lancet cover, and a pricking element, the lancet body being connected to the lancet cover, and the pricking element being disposed within the lancet body and the lancet cover such that a sharp tip portion of the pricking element is encapsulated by the lancet cover and such that the pricking element extends between the lancet body and the lancet cover, the lancet cover including a tapered portion, and wherein the lancet structure is configured to be inserted into a lancet holder such that the base moves toward the connector and the spring is compressed, and such that the lancet cover is separated from the pricking element by movement in an oblique direction of the lancet cover by the tapered portion of the lancet cover being moved along a reverse tapered portion of the lancet holder, relative to the pricking element, which remains substantially in the same position, thereby exposing the encapsulated sharp tip portion of the pricking element.

32. The lancet assembly according to claim 26, wherein the pricking element is disposed in the lancet cover, and the lancet cover is arranged so as to be displaced laterally relative to a longitudinal direction of the pricking element when the spring is compressed so as to enable the pricking element to pass through an opening in the lancet holder.

33. The lancet assembly according to claim 27, wherein the pricking element is disposed in the lancet cover, and the lancet cover is arranged so as to be displaced laterally relative to a longitudinal direction of the pricking element when the spring is compressed so as to enable the pricking element to pass through the opening in the lancet holder.

34. The lancet assembly according to claim 28, wherein the pricking element is disposed in the lancet cover, and the lancet cover is arranged so as to be displaced laterally relative to a longitudinal direction of the pricking element when the spring is compressed so as to enable the pricking element to pass through an opening in the lancet holder.

35. The lancet assembly according to claim 29, wherein the pricking element is disposed in the lancet cover, and the lancet cover is arranged so as to be displaced laterally relative to a longitudinal direction of the pricking element when the spring is compressed so as to enable the pricking element to pass through an opening in the lancet holder.

36. The lancet assembly according to claim 30, wherein the pricking element is disposed in the lancet cover, and the lancet cover is arranged so as to be displaced laterally relative to a longitudinal direction of the pricking element when the spring is compressed so as to enable the pricking element to pass through the opening in the lancet holder.

37. The lancet assembly according to claim 31, wherein the pricking element is disposed in the lancet cover, and the lancet cover is arranged so as to be displaced laterally relative to a longitudinal direction of the pricking element when the spring is compressed so as to enable the pricking element to pass through an opening in the lancet holder.

* * * * *